United States Patent [19]

Shephard

[11] 4,340,538

[45] Jul. 20, 1982

[54] PROCESS FOR PRODUCING 6α-FLUORO-Δ$^{1,4}$-3-KETO STEROIDS

[75] Inventor: Kenneth P. Shephard, Portage, Mich.

[73] Assignee: The Upjohn Company, Kalamazoo, Mich.

[21] Appl. No.: 170,790

[22] Filed: Jul. 21, 1980

[51] Int. Cl.$^3$ ............................................. C07J 71/00
[52] U.S. Cl. ...................... 260/239.55 D; 260/397.45; 260/397.3; 260/239.55 R
[58] Field of Search ..................... /Steroids MS File; 260/397.45, 239.55 D

[56] References Cited

U.S. PATENT DOCUMENTS

| | | | |
|---|---|---|---|
| 2,838,537 | 6/1958 | Spero et al. | 260/397.45 |
| 2,838,538 | 6/1958 | Spero et al. | 260/397.45 |
| 2,838,542 | 6/1958 | Spero et al. | 260/397.45 |
| 2,838,543 | 6/1958 | Spero et al. | 260/397.45 |
| 2,841,600 | 7/1958 | Hogg et al. | 260/397.45 |
| 2,876,219 | 3/1959 | Campbell et al. | 260/239.55 |
| 2,877,240 | 3/1959 | Campbell et al. | 260/397.4 |
| 2,880,205 | 3/1959 | Campbell et al. | 260/239.55 |
| 2,989,523 | 6/1961 | Beal et al. | 260/239.55 |
| 3,004,044 | 10/1961 | Campbell et al. | 260/397.3 |
| 3,127,428 | 3/1964 | Tanabe et al. | 260/397.4 |
| 3,127,430 | 3/1964 | Shapiro et al. | 260/397.4 |
| 3,221,033 | 11/1965 | Shapiro | 260/397.4 |
| 3,239,540 | 3/1966 | Campbell et al. | 260/397.3 |
| 3,332,967 | 7/1967 | Oliveto et al. | 260/397.45 |
| 4,011,315 | 3/1977 | Marx et al. | 260/239.55 D |
| 4,198,403 | 4/1980 | Alvarez | 260/239.5 |

FOREIGN PATENT DOCUMENTS 1052223  12/1966  United Kingdom ........... 260/397.45

*Primary Examiner*—Elbert L. Roberts
*Attorney, Agent, or Firm*—Bruce Stein

[57] ABSTRACT

Two processes are disclosed (one-pot and two-pot) for the transformation of a 6β-fluoro-Δ$^{1,4}$-3-keto steroid (IV) to a 6α-fluoro-Δ$^{1,4}$-3-keto steroid (VI). These processes permit the introduction of a fluorine atom at the 6α position of a Δ$^{1,4}$-3-keto steroid where previously the Δ$^1$ double bond could not be introduced until after the 6α-fluorine atom was present. The 6α-fluoro-Δ$^{1,4}$-3-keto steroids (VI) are intermediates useful in the production of pharmacologically active steroids.

46 Claims, No Drawings

PROCESS FOR PRODUCING 6α-FLUORO-Δ$^{1,4}$-3-KETO STEROIDS

BACKGROUND OF THE INVENTION

Diflorasone diacetate, fluocortolone, fluocinolone acetonide, fluocinonide, paramethasone and fluprednisolone are 6α-fluoro-Δ$^{1,4}$-3-keto steroids which are of pharmacological value primarily as topical anti-inflammatory agents.

Present technology requires that the production of these 6α-fluoro-Δ$^{1,4}$-3-keto steroids necessitates the epimerization of the 6β-fluoro group of a steroid prior to Δ$^1$-dehydrogenation. See, for example, U.S. Pat. Nos. 3,980,778, 3,014,938 and 3,126,375 and J. Am. Chem. Soc. 82, 4001 (1960).

It would be highly desirable to be able to epimerize a fluorine atom at the 6β-position in a Δ$^{1,4}$-3 keto steroid. However, prior to the present invention there was no known procedure for accomplishing this process.

Others have reported that they have attempted to do this but were unsuccessful. For example, D. H. R. Barton et al. reported in Nouveau Journal De Chimie 1, 315 (1977) an unsuccessful attempt to epimerize a flourine atom at the 6β-position in a Δ$^{1,4}$-3-keto steroid. Barton tried epimerization of a 6β-fluoro-Δ$^{1,4}$-3-keto steroid by use of triphenylmethyl lithium. Instead of obtaining epimerization he obtained elimination of the fluorine atom. The present invention overcomes this problem.

H. J. Ringold and S. K. Malhotra in Tetrahedron Letters 669 (1972) reported deconjugation of a Δ$^4$-3-keto steroid. However, the authors reported they were unable to deconjugate a Δ$^{1,4}$-3-keto steroid, see page 672.

E. L. Shapiro et al. in Steroids 3, 183 (1964) reported deconjugation of a Δ$^{1,4}$-3-keto steroid to give a Δ$^{1,5}$-3-keto steroid. However, the reactant did not contain a fluorine atom at C-6. Barton, supra, reported an attempt to deconjugate a 6β-fluoro-Δ$^{1,4}$-3-keto steroid. He reported that instead of obtaining deconjugation he obtained elimination. The present invention has solved this problem and permits deconjugation of 6β-fluoro-Δ$^{1,4}$-3-keto steroids.

U.S. Pat. No. 4,188,322 claims a process for introduction of a fluorine atom in the 6α-position of a 9β,11β-epoxy-Δ$^{1,4}$-3-keto steroid by first forming the corresponding 3-enol derivative by acylation or etherification followed by reaction with a suitable halogenating agent.

Great Britain Pat. No. 2,018,258 discloses virtually the same process as does U.S. Pat. No. 4,188,322.

Both U.S. Pat. No. 4,188,322 and Great Britain Pat. No. 2,018,258 differ from the process of the present invention in that these processes introduce a fluorine atom into the steroid at the C$_6$ position directly in the α configuration while the process of the present invention introduces a fluorine atom at the C$_6$ position in the opposite or β configuration followed by epimerization to the α position. In addition, the process of the present invention advantageously does not require that the C$_3$ keto group be protected as an enol ether or ester.

Polish Pat. No. 85,557 discloses a process for isomerization of a 6β-fluoro-Δ$^{1,4}$-3-keto-11-oxygenated steroid to the corresponding 6α-fluoro-Δ$^{1,4}$-3-keto-11-oxygenated steroid by use of isomerizing agents which are acids. In the process of the present invention the transformation of the 6β-fluoro-Δ$^{1,4}$-3-keto steroid (IV) to the corresponding 6α-fluoro-Δ$^{1,4}$-3-keto steroid is accomplished by a basic agent not an acidic one. In addition, the process of the present invention does not require an 11-oxygenated steroid.

BRIEF DESCRIPTION OF THE INVENTION

A process for preparing a 6α-fluoro-Δ$^{1,4}$-3-keto steroid of formula VI which comprises (1) deconjugating a 6β-fluoro-Δ$^{1,4}$-3-keto steroid of formula IV by reaction with a deconjugating agent, (2) quenching with a quenching agent to produce a 6-fluoro-Δ$^{1,5}$-3-keto steroid of formula V, (3) isolating the 6-fluoro-Δ$^{1,5}$-3-keto steroid (V), (4) isomerizing the 6-fluoro-Δ$^{1,5}$-3-keto steroid (V) by reaction with an isomerizing agent and (5) neutralizing with an acid where R$_9$ and $\overline{\phantom{---}}$ are defined as hereinafter.

A process for preparing a 6-fluoro-Δ$^{1,5}$-3-keto steroid of formula V is also disclosed.

DETAILED DESCRIPTION OF THE INVENTION

The processes of the present invention permits the epimerization of a fluorine atom at the 6β-position of Δ$^{1,4}$-3-keto steroid to the 6α-fluoro epimer. Most topical anti-inflammatory agents are Δ$^{1,4}$-3-keto steroids and some also have a 6α-fluorine atom. Prior to the present invention the fluorine atom at the 6α-position of a 6α-fluoro-Δ$^{1,4}$-3-keto steroid had to be introduced into the steroid prior to the Δ$^1$ double bond. The present invention therefore permits greater flexibility in the synthesis of 6α-fluoro-Δ$^{1,4}$-3-keto steroids.

Chart A discloses that the very common Δ$^{1,4}$-3-keto steroids can be transformed to the 6β-fluoro-Δ$^{1,4}$-3-keto (IV) starting material by methods well known to those skilled in the art. The Δ$^{1,4}$-3-keto steroid is deconjugated to the corresponding Δ$^{1,5}$-3-keto steroid (II) followed by halogenation with an N-haloamide and hydrogen fluoride to give the 5α-halo-6β-fluoro-3-keto steroid (III) which upon elimination produces the desired 6β-fluoro-Δ$^{1,4}$-3-keto (IV) starting material. In addition, the 6β-fluoro-Δ$^{1,4}$-3-keto steroids (IV) are well known to those skilled in the art, see for example, D. H. R. Barton, Nouveau Journal De Chimie 1,315 (1977) and R. H. Hesse, Israel Journal of Chemistry 17, 60 (1978).

The 6β-fluoro-Δ$^{1,4}$-3-keto steroid (IV) diagrams show not the entire steroid molecule but primarily rings A and B, since this is where the process of the present invention takes place. The $\cdots$ in ring C between C$_9$ and C$_{11}$ means that ring C can have the following types of substitution: 9β,11β-epoxy, Δ$^{9(11)}$, 11β-hydroxy, 11-keto 11α-hydroxy, 9α-fluoro-11β-hydroxy and no substitution (hydrogen atoms at C$_9$ and C$_{11}$). It is preferred that the ring C substitution be 9β,11β-epoxy or Δ$^{9(11)}$. It is more preferred that the substitution be 9β,11β-epoxy. Likewise, the chemical formula diagrams for the 6β-fluoro-Δ$^{1,4}$-3-keto steroid (IV) does not disclose ring D or C$_{17}$ side chain. This is because there are a large number of different ring D and C$_{17}$ side chain variations that are operable, see for example Chart E. The important point is that the hydroxyl groups, when present, at C$_{16}$, C$_{17}$, C$_{20}$, and/or C$_{21}$ be protected as disclosed in Chart E. The use (formation and removal) of hydroxyl protecting groups is well known to those skilled in the art.

The 6β-fluoro-Δ$^{1,4}$-3-keto steroid (IV) can be transformed to the desired 6α-fluoro-Δ$^{1,4}$-3-keto steroid (VI) by two different but similar processes. One is a one-pot process which can be performed in either 2 or 3 steps involving epimerization followed by neutralization of the base by acid. The other is a two-pot process where the first step involves deconjugation of the 6β-fluoro-$\Delta^{1,4}$-3-keto steroid (IV) followed by quenching which permits isolation of the 6-fluoro-$\Delta^{1,5}$-3-keto intermediate (V) followed by isomerization to the 6α-fluoro-$\Delta^{1,4}$-3-keto steroid (VI).

In the two-pot process (Chart A), the 6β-fluoro-$\Delta^{1,4}$-3-keto steroid is deconjugated by reaction with a deconjugating agent which is a strong base selected from the group consisting of $ORb^\ominus$, acetylide or $R\alpha R\beta N^\ominus$, or a means of producing $ORb^\ominus$ acetylide or $R\alpha R\beta N^\ominus$. Rb is alkyl of 1 thru 4 carbon atoms. Rα and Rβ are the same or different and are a hydrogen atom, alkyl of 1 thru 4 carbon atoms, cyclohexyl or phenyl. It is preferred that the deconjugating agent is selected from the group consisting of methoxide, ethoxide or tert-butoxide. Preferred dialkylamides include diethylamide and diisopropylamide. A means for producing $ORb^\ominus$ etc. is included because if a strong base not within the scope of the deconjugating agents is used in methanol, the actual species in situ will be methoxide generated from the methanol by the strong base. Generating a deconjugating agent in situ is equivalent to mixing one with the 6β-fluoro-$\Delta^{1,4}$-3-keto steroid (IV). In general an aprotic solvent is used for the deconjugating reaction. The aprotic solvent is used so as not to protonate the intermediate enolate generated by the deconjugating agent. Preferred solvents include for example THF, DMSO, dioxane, DMF, tetramethylurea, dimethylacetamide and tert-butanol. Both tert.-butanol and tert-amyl alcohol are protic solvents but they do not protonate the enolate so they are suitable. When the solvent is tert-butanol, about 10 equivalents of deconjugating agent-/equivalent of steroid is preferred. If less is used, there is a cost savings but the reaction time will be longer. If greater than 10 equivalents are used, the reaction is more costly but proceeds at a more rapid rate. After deconjugation the reaction is quenched by reaction with a quenching agent which is a compound that will supply a proton and protonate the enolate. Quenching agents include, for example, acetic acid, aqueous ammonium chloride, sulfuric acid, hydrochloric acid, phosphoric acid and water. It is more preferred that the quenching agent be acetic acid or aqueous ammonium chloride. Following quenching the 6-fluoro-$\Delta^{1,5}$-3-keto intermediate (V) can be isolated if desired. The 6-fluoro-$\Delta^{1,5}$-3-keto intermediate (V) is useful in producing and is isomerized to 6α-fluoro-$\Delta^{1,4}$-3-keto steroid (VI) by reaction with an isomerizing agent. Isomerizing agents include compounds selected from the group consisting of $ORb^\ominus$ or hydroxide or a means of producing $ORb^\ominus$ or hydroxide. A means for producing $ORb^\ominus$ or hydroxide is included because use of sodium diethylamide in methanol actually produces methoxide in situ and therefore is an equivalent of methoxide. The isomerizing agent removes a proton, isomerization takes place and the steroid obtains a proton from the protic solvent. Hence, preferred agents include methoxide in methanol and ethoxide in ethanol. This two-pot process is performed at 20°–25° and can be monitored by TLC as exemplified in Examples 1 and 2.

The isomerizing agent is neutralized with an acid. It is preferred that the acid be selected from the group consisting of acetic, hydrochloric, sulfuric, phosphoric and ammonium chloride. Alternatively, instead of neutralization of the isomerizing agent, the reaction mixture can be diluted with water and the steroid recovered as is well known to those skilled in the art such as by filtration or extraction.

The 6β-fluoro-$\Delta^{1,4}$-3-keto steroid (IV) can be epimerized to the desired 6α-fluoro-$\Delta^{1,4}$-3-keto steroid (VI) in a one-pot process either in three steps or by two steps. The three-step process involves reaction of the 6β-fluoro-$\Delta^{1,4}$-3-keto steroid (IV) with an deconjugating agent in the presence of a solvent selected from the group consisting of THF, DMSO, DMF, diethylacetamide, dioxane, tert-butanol and tert-amyl alcohol. The deconjugating agent is selected from the group consisting of $ORb^\ominus$, acetylide and $R\alpha R\beta N^\ominus$ or a means of producing $ORb^\ominus$, acetylide or $R\alpha R\beta N^\ominus$. It is preferred that the deconjugating agent is methoxide, ethoxide or tert-butoxide. Following the reaction of the steroid (IV) and the deconjugating agent, a primary or secondary alcohol of the formula Rb-OH is mixed with the steroid reaction mixture. The reaction of the deconjugating agent and the primary or secondary alcohol (Rb-OH) forms an isomerizing agent in situ. When the reaction is complete, the base is neutralized by reaction with an acid preferably selected from the group consisting of acetic, hydrochloric, sulfuric, phosphoric and ammonium chloride. Instead of neutralization the reaction mixture can be diluted as explained previously.

Alternatively, the one-pot process can be performed in two steps. First, the steroid (IV) is mixed with the deconjugating agent in the presence of a primary or secondary alcohol (Rb-OH) followed by neutralization with an acid or dilution with water as explained previously.

In both the one-pot processes, the reaction is performed at 20°–25° and is monitored by TLC.

In both the two-pot and one-pot processes disclosed in Chart A for the transformation of the 6β-fluoro-$\Delta^{1,4}$-3-keto steroid (IV) to the desired 6α-isomer (VI) it is preferred that the substitution in ring C be the 9β,11-epoxide or $\Delta^{9(11)}$. It is more preferred that the substitution be 9β,11β-epoxy, since for some unknown and unexpected reason the reactions proceed much faster. For example, the epimerization reaction of a 9β,11β-epoxide (IV) in methanol (methoxide) is complete in 2–4 hours, whereas if the 9β,11β-epoxide is absent, the same reaction takes about 80–90 hours.

The processes of the present invention are useful in producing a 6α-fluoro-$\Delta^{1,4}$-3-keto steroid (VI) from a 6β-fluoro-$\Delta^{1,4}$-3-keto steroid (IV) which can readily be obtained from the readily available $\Delta^{1,4}$-3-keto steroids (I).

The 6α-fluoro-$\Delta^{1,4}$-3-keto steroid (IV) functionality is common to a number of steroids which are useful because of their topical anti-inflammatory activity. These topically anti-inflammatory steroids include, for example, diflorasone diacetate, fluocinonide, fluocinolone acetonide, paramethasone, fluprednisolone and fluocortolone. The introduction of the various functionalites of these compounds such as 11α-hydroxy, 16α-hydroxy or 9α-fluoro groups, acetonide formation, transformation of $\Delta^{9(11)}$ to 9α-fluoro-11β-hydroxy can take place either before or after the introduction of the 6α-fluoro group as is well known to those skilled in the art.

For example, starting with 6β-fluoro-17α,20,21-trihydroxy-16β-methylpregna-1,4,9(11)-trien-3-one 20,21-acetonide (IV') the process of the present invention produces 6α-fluoro-17α,20,21-trihydroxy-16β-methylpregna-1,4,9(11)-trien-3-one 20,21-acetonide (VI'), see Examples 1 thru 2a. By known process chemistry (Chart B) this 6α-fluoro-$\Delta^{1,4}$-3-keto (VI') steroid is converted to diflorasone diacetate (U.S. Pat. No. 3,980,778) which is a commercially marketed topical anti-inflammatory agent. The acetonide is removed (U.S. Pat. No. 3,725,392, Examples 9–11) to form the 20,21-dihydroxy steroid (VII'); the 21-benzoate (VIII') is formed (U.S. Pat. No. 3,725,392, Example 12); the 20-hydroxyl is oxidized to the 20-keto steroid (IX') by the process of U.S. Pat. No. 3,725,392, Example 13; the 11β-hydroxy-9α-bromo compound (X') is formed (U.S. Pat. No. 3,725,392, Example 15); the epoxide (XI') is formed (U.S. Pat. No. 3,725,392, Example 16); the orthoester (XII') is formed (U.S. Pat. No. 3,147,249); which permits formation of the 17-acetate (XIII') by the process of U.S. Pat. No. 3,152,154 and formation of the diacetate (XIV') by very well known methods and opening of the epoxide by the process of Example 8 of U.S. Pat. No. 3,980,778 to give diflorasone diacetate (XV).

Utilizing the generic process (Chart A), Chart B discloses the usefulness of a particular 6α-fluoro-$\Delta^{1,4}$-3-keto steroid (VI') when the process of the present invention is performed on a steroid where the C ring has a $\Delta^{9(11)}$-functionality. Subsequent to the transformation of the 6β-fluoro atom to a 6α-fluoro atom, the $\Delta^{9(11)}$-double bond is transformed by the usual method to the bromohydrin (X'), the epoxide (XI') and subsequently to the desired 9α-fluoro-11β-hydroxy C ring functionality (XV'). Chart C discloses generically the process of the present invention where the process is performed on a 9β,11β-epoxide (E) functionality in the C ring.

One of the products desired to be produced by the processes of the present invention is diflorasone diacetate, 6α,9α-difluoro-11β,17α,21-trihydroxy-16β-methylpregna-1,4-diene-3,20-dione 17,21-diacetate (XV'). The starting material would be 6β-fluoro-17α,20,21-trihydroxy-16β-methylpregna-1,4,9(11)-trien-3-one 20,21-acetonide (IV').

To produce diflorasone diacetate (XV') from the starting material (IV') by the process of Charts A and B, the 6-fluorine atom is epimerized (V and VI) to give the desired 6α-fluoro-$\Delta^{1,4}$-3-keto functionality of rings A and B and then (Chart B) the side chain is modified to the desired 17α,21-dihydroxy-20-one (VI'-IX'), the $\Delta^{9(11)}$ double bond is transformed to the 9β,11β-epoxide (IX'-XI'), the side chain is transformed to final form, 17α,21-dihydroxy-20-one 17,21-diacetate (XI'-XIV') and the epoxide is opened to give the desired 9α-fluoro-11β-hydroxy ring C functionality (XIV'-XV').

To produce the same diflorasone diacetate (XV') from the same starting material (IV') by the process of Chart C, the process of Chart D is followed, the side chain is modified to the desired 17α,21-dihydroxy-20-one 21-acylate (IV'-IXβ'), the $\Delta^{9(11)}$ double bond is transformed to the 9β,11β-epoxide (IXβ'-E') and the 21-ester of the side chain is hydrolyzed to give (XI'), which is exactly the same compound of Chart B, see Example 12. Compound (XI') is then transformed to diflorasone diacetate in the identical manner as in Chart B. Hence, the starting material (IV') can be transformed to diflorosone diacetate (XV') two different ways, by the processes of the present invention. These two processes overlap somewhat in that the end portion (XI'-XV') is identical; the beginning portion differs in that in one process the epoxide is formed prior to epimerization, while in the alternative process, the 6β-fluorine atom is epimerized prior to the epoxide formation. Both processes produce the desired result.

DEFINITIONS

The definitions and explanations below are for the terms as used throughout the entire patent application including both the specification and claims.

All temperatures are in degrees Centigrade.
TLC refers to thin-layer chromatography.
THF refers to tetrahydrofuran.
THP refers to tetrahydropyranyl.
DMSO refers to dimethylsulfoxide.
DMF refers to dimethylformamide.
SSB refers to an isomeric mixture of hexanes.
DMAC refers to dimethylacetamide.
Saline refers to an aqueous saturated sodium chloride solution.
When solvent pairs are used, the ratio of solvents used are volume/volume (v/v).
R is methyl or ethyl.
$R_5$ is a chlorine or bromine atom.
$R_9$ is a hydrogen or fluorine atom.
$R_{16}$ is a hydrogen atom or methyl or hydroxyl group.
$R_{17}$ is methyl or phenyl.
$R_{21}$ is methyl or phenyl.
Rb is alkyl of 1 thru 5 carbon atoms.
Rα refers to a hydrogen atom, alkyl of 1–4 carbon atoms, cyclohexyl and phenyl.
Rβ refers to a hydrogen atom, alkyl of 1–4 carbon atoms, cyclohexyl and phenyl.
~ indicates the attached group can be in either the α or β configuration.
--- is a single (no substitution) or double bond [$\Delta^{9(11)}$], 9β,11β-epoxy, 11-keto or 11β-hydroxy.
When the term "alkyl of __ thru __ carbon atoms" is used, it means and includes isomers thereof where such exist.

EXAMPLES

Without further elaboration, it is believed that one skilled in the art can, using the preceding description, practice the present invention to its fullest extent. The following preferred specific embodiments are, therefore, construed as merely illustrative, and not limiting of the preceding disclosure in any way whatsoever.

Example 1

6-Fluoro-17α,20,21-trihydroxy-16β-methylpregna-1,5,9(11)-trien-3-one 20,21-acetonide (V)

A mixture of 6β-fluoro-17α,20,21-trihydroxy-16β-methylpregna-1,4,9(11)-trien-3-one 20,21-acetonide (IV, 1.0 g.) and tertiary butyl alcohol (25 ml.) is stirred at 20°–25° under nitrogen. A solution of potassium tertiary butoxide (20%, 16 ml.) is added to the above mixture, which is then stirred at 20°–25° while monitoring the reaction by TLC. After stirring for 90 minutes the reaction mixture is treated with aqueous acetic acid (20%, 63 ml.) and is then transferred to a separatory funnel containing water (100 ml.). This mixture is extracted with ethyl acetate (2×50 ml.). The ethyl acetate extracts are combined, washed wth aqueous potassium bicarbonate (10%, 2×100 ml.) washed with water (100 ml.), washed with half saturated aqueous sodium chloride solution (80 ml.), dried over anhydrous magnesium sulfate and evaporated to dryness under reduced pressure, while warming at 50°. The residue is treated with acetone and the resulting slurry filtered. The solids are washed with cold acetone and dried under reduced pressure at 70° to give the title compound, m.p. 188°–192°.

Example 2

6α-Fluoro-17α,20,21-trihydroxy-16β-methylpregna-1,4,9(11)-trien-3-one 20,21-acetonide (VI')

A slurry of 6-fluoro-17α,20-21-trihydroxy-16β-methylpregna-1,5,9-(11)-trien-3-one 20,21-acetonide (V, Example 1, 0.40 g.) in methanol (10 ml.) is treated with sodium methoxide (0.010 g.) and stirred under nitrogen at 20°–25°. The reaction is monitored by TLC. After stirring for 80 minutes the reaction mixture is quenched by the addition of a solution of acetic acid (10%) in methanol. This slurry is concentrated to a small volume by reduced pressure. The thick slurry is cooled and filtered. The solids are washed quickly with methanol cooled to 0° and dried under reduced pressure at 60° to give the title compound, m.p. 232°–234°.

Example 2a

6α-Fluoro-17α,20,21-trihydroxy-16β-methylpregna-1,4,9(11)-trien-3-one 20,21-acetonide (VI')

A mixture of 6β-fluoro-17α,20,21-trihydroxy-16β-methylpregna-1,4,9(11)-trien-3-one 20,21-acetonide (IV, 1.0 g.) in methanol (24 ml.) is stirred at 20°–25°. Potassium t-butoxide (14.5 ml.) in THF is added and stirred. After 24 hours, a 50:50 mixture of the product (VI) and starting material (IV) are observed by TLC. After 90 hours, the reaction is greater than 95% complete as measured by TLC. The reaction mixture is then worked up as in Example 2.

Example 3

6α-Fluoro-17α,20,21-trihydroxy-16β-methylpregna-1,4,9(11)-trien-3-one (VII')

Following the procedure of U.S. Pat. No. 3,725,392 in general and more particularly the procedure of Examples 9–11 and making non-critical variations but starting with 6α-fluoro-17α,20,21-trihydroxy-16β-methylpregna-1,4,9(11)-trien-3-one 20,21-acetonide (VI', Example 2) the title compound is obtained.

Example 3a

6α-Fluoro-17α,20,21-trihydroxy-16β-methylpregna-1,4,9(11)-trien-3-one (VII')

A mixture of 6β-fluoro-17α,20,21-trihydroxy-16β-methylpregna-1,4,9(11)-trien-3-one 20,21-acetonide (IV, 30 g.), THF (90 ml.) and t-butyl alcohol (30 ml.) is stirred at 20°–25°. Potassium t-butoxide in THF (20%, 105 ml.) is added and the mixture stirred. After 10 minutes, the reaction mixture is cooled to 15°. Methanol (60 ml) is added while allowing the reaction temperature to rise to 25°.

The mixture is stirred for 15 minutes and then concentrated hydrochloric acid (15 ml.) in water (60 ml.) is added and the mixture refluxed for one hour. Water (60 ml.) is added and the mixture is concentrated under reduced pressure to a volume of 30 ml. This slurry is cooled to 0°–5° and filtered. The solids are washed with four 60 ml. portions and one 100-ml. portion of water. The solids are dried under reduced pressure at 50° to give the title compound.

Example 4

6α-Fluoro-17α,20,21-trihydroxy-16β-methylpregna-1,4,9(11)-trien-3-one 21-benzoate (VIII')

Following the procedure of U.S. Pat. No. 3,725,392 in general and more particularly the procedure of Example 12 and making non-critical variations but starting with 6α-fluoro-17α,20,21-trihydroxy-16β-methylpregna-1,4,9(11)-trien-3-one (VII', Example 3) the title compound is obtained.

Example 5

6α-Fluoro-17α,21-dihydroxy-16β-methylpregna-1,4,9(11)-triene-3,20-dione 21 benzoate (IX')

Following the procedure of U.S. Pat. No. 3,725,392 in general and more particularly the procedure of Example 13 and making non-critical variations but starting with 6α-fluoro-17α,20,21-trihydroxy-16β-methylpregna-1,4,9(11)-trien-3-one 21-benzoate (VII', Example 4) the title compound is obtained.

Example 6

9α-Bromo-6α-fluoro-11β,17α,21-trihydroxy-16β-methyl-pregna-1,4-diene-3,20-dione 21-benzoate (X')

Following the procedure of U.S. Pat. No. 3,725,392 in general and more particularly the procedure of Example 15 and making non-critical variations but starting with 6α-fluoro-17α,21-dihydroxy-16β-methylpregna-1,4,9(11)-triene-3,20-dione 21-benzoate (IX', Example 5) the title compound is obtained.

Example 7

6α-Fluoro-17α,21-dihydroxy-16β-methyl-9β,11β-oxidopregna-1,4-diene-3,20-dione (XI')

Following the procedure of U.S. Pat. No. 3,725,392 in general and more particularly the procedure of Example 16 and making non-critical variations but starting with 9α-bromo-6α-fluoro-11β,17α,21-trihydroxy-16β-methylpregna-1,4-diene-3,20-dione 21-benzoate (X', Example 6) the title compound is obtained.

Example 8

17α,21-(1'-Methoxy)-ethylidenedioxy-6α-fluoro-16β-methyl-9β,11β-oxidopregna-1,4-diene-3,20-dione (XII')

Following the general procedure of U.S. Pat. No. 3,147,249 and making non-critical variations and reacting 6α-fluoro-17α,21-dihydroxy-16β-methyl-9β,11β-oxidopregna-1,4-diene-3,20-dione (XI', Example 7) with methyl orthoacetate the title compound is obtained.

Example 9

6α-Fluoro-17α,21-dihydroxy-16β-methyl-9β,11β-oxidopregna-1,4-diene-3,20-dione 17-acetate (XIII')

Following the general procedure of U.S. Pat. No. 3,152,154 and making non-critical variations but hydrolyzing 17α,21-(1'-methoxy)-ethylidenedioxy-6α-fluoro-16β-methyl-9β,11β-oxidopregna-1,4-diene-3,20-dione (XII', Example 8) the title compound is obtained.

Example 10

6α-Fluoro-17α,21-dihydroxy-16α-methyl-9β,11β-oxidopregna-1,4-diene-3,20-dione 17,21-diacetate (XIV')

6α-Fluoro-17α, 21-dihydroxy-16β-methyl-9β,11β-oxidopregna-1,4-diene-3,20 -dione 17-acetate (XIII', Example 9) is heated with acetyl chloride and pyridine to give the title compound.

Example 11

6α,9α-Difluoro-11β,17α,21-trihydroxy-16β-methylpregna-1,4-diene-3,20-dione 17,21-diacetate (XV', U.S. Pat. No. 3,980,778).

Following the procedure of Example 8 of U.S. Pat. No. 3,980,778, 6α-fluoro-17α,21-dihydroxy-16β-methyl-9β,11β-oxidopregna-1,4-diene-3,20-dione 17,21-diacetate (XIV', Example 10) is converted to the title compound.

Example 12

6α-Fluoro-17α,21-dihydroxy-16β-methyl-9β,11β-oxidopregna-1,4-diene-3,20-dione (XI')

Step 1: 6β-Fluoro-17α,20,21-trihydroxy-16β-methylpregna-1,4,9(11)-trien-3-one (VIIβ')

Following the general procedure of Example 3 and making non-critical variations but starting with 6β-fluoro-17α,20,21-trihydroxy-16β-methylpregna-1,4,9(11)-trien-3-one-20,21-acetonide (IV'), 6β-fluoro-17α,20,21-trihydroxy-16β-methylpregna-1,4,9(11)-trien-3-one is obtained.

Step 2: 6β-Fluoro-17α,20,21-trihydroxy-16β-methylpregna-1,4,9(11)-trien-3-one 21-benzoate (VIIβ')

Following the general procedure of Example 7 and making non-critical variations but starting with 6β-fluoro-17α,20,21-trihydroxy-16β-methylpregna-1,4,9(11)-trien-3-one (VIIβ', Step 1), 6β-fluoro-17α,20,21-trihydroxy-16β-methylpregna-1,4,9(11)-trien-3-one 21-benzoate is obtained.

Step 3: 6β-Fluoro-17α,21-dihydroxy-16β-methylpregna-1,4,9(11)-triene-3,20-dione 21-benzoate (IXβ')

Following the general procedure of Example 8 and making non-critical variations but starting with 6β-fluoro-17α,20,21-trihydroxy-16β-methylpregna-1,4,9(11)-trien-3-one 21-benzoate (VIIIβ', Step 2), 6β-fluoro-17α,21-dihydroxy-16β-methylpregna-1,4,9(11)-triene-3,20-dione is obtained.

Step 4: 9α-Bromo-6β-fluoro-11β,17α,21-trihydroxy-16β-methylpregna-1,4-diene-3,20-dione 21-benzoate (Xβ')

Following the general procedure of Example 9 making non-critical variations but starting with 6β-fluoro-17α,21-dihydroxy-16β-methylpregna-1,4,9(11)-triene-3,20-dione 21-benzoate (IXβ', Step 3), 9α-bromo-6β-fluoro-11β,17α,21-trihydroxy-16β-methylpregna-1,4-diene-3,20-dione 21-benzoate is obtained.

Step 5: 6α-Fluoro-17α,21-dihydroxy-16β-methyl-9β,11β-oxidopregna-1,4-diene-3,20-dione (XI')

9α-Bromo-6β-fluoro-11β,17α,21-trihydroxy-16β-methylpregna-1,4-diene-3,20-dione 21-benzoate (Xβ', Step 4) is stirred with methylene chloride (106 ml.) and methanol (222 ml.) at 3°. A solution of potassium tert-butoxide in THF (20%, 57.5 ml.) is added to the steroid mixture and the temperature rises from 3° to 11°. After stirring for 1.75 hours, the reaction mixture is warmed to 20°–25° and the epimerization appears complete as measured by TLC. The reaction is quenched by the addition of glacial acetic acid. The slurry is concentrated to a volume of 164 ml. Water (100 ml.) is added and the resulting slurry is concentrated under reduced pressure to 164 ml. Water (431 ml.) is added slowly and the resulting slurry is cooled to 5° and filtered. The solids are washed with water and dried under vacuum at 55° to give the title compound.

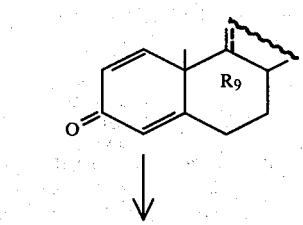

I

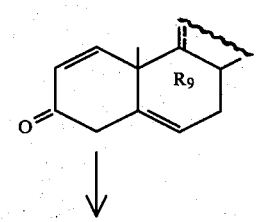

II

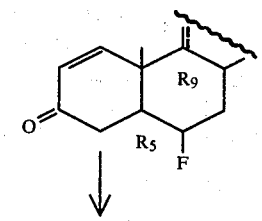

III

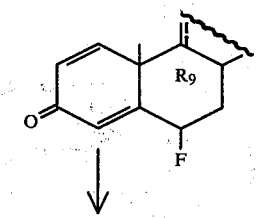

IV

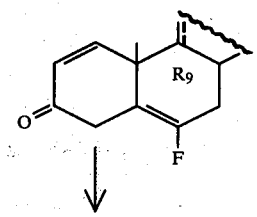

V

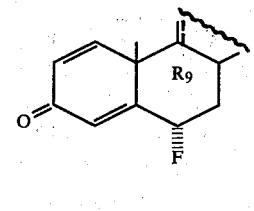

VI

CHART B

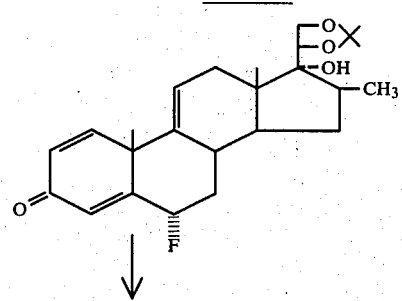

(VI')

-continued
CHART B
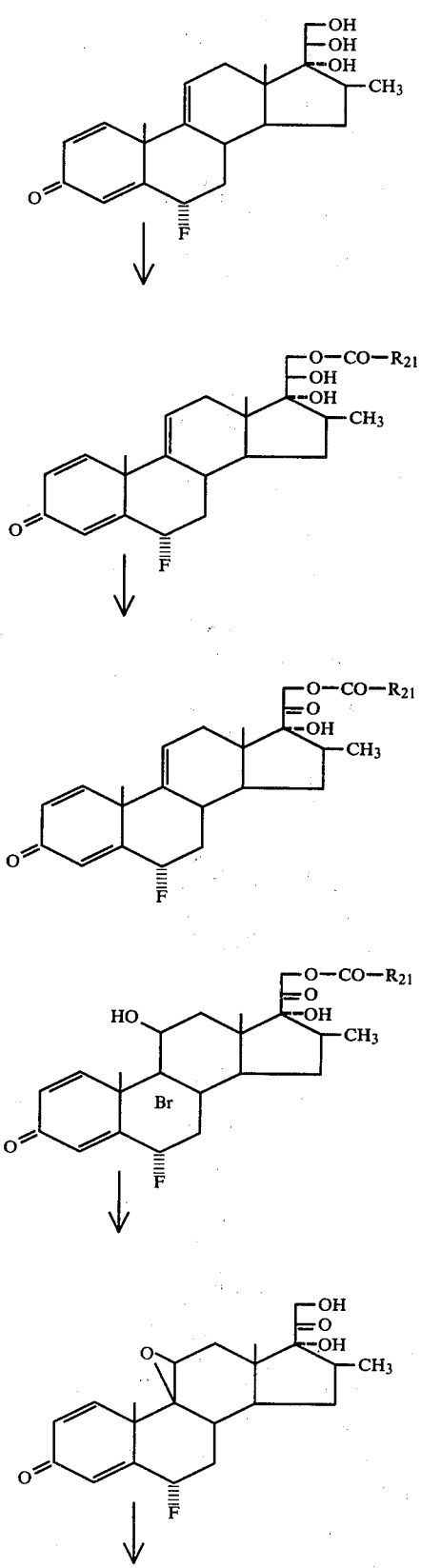
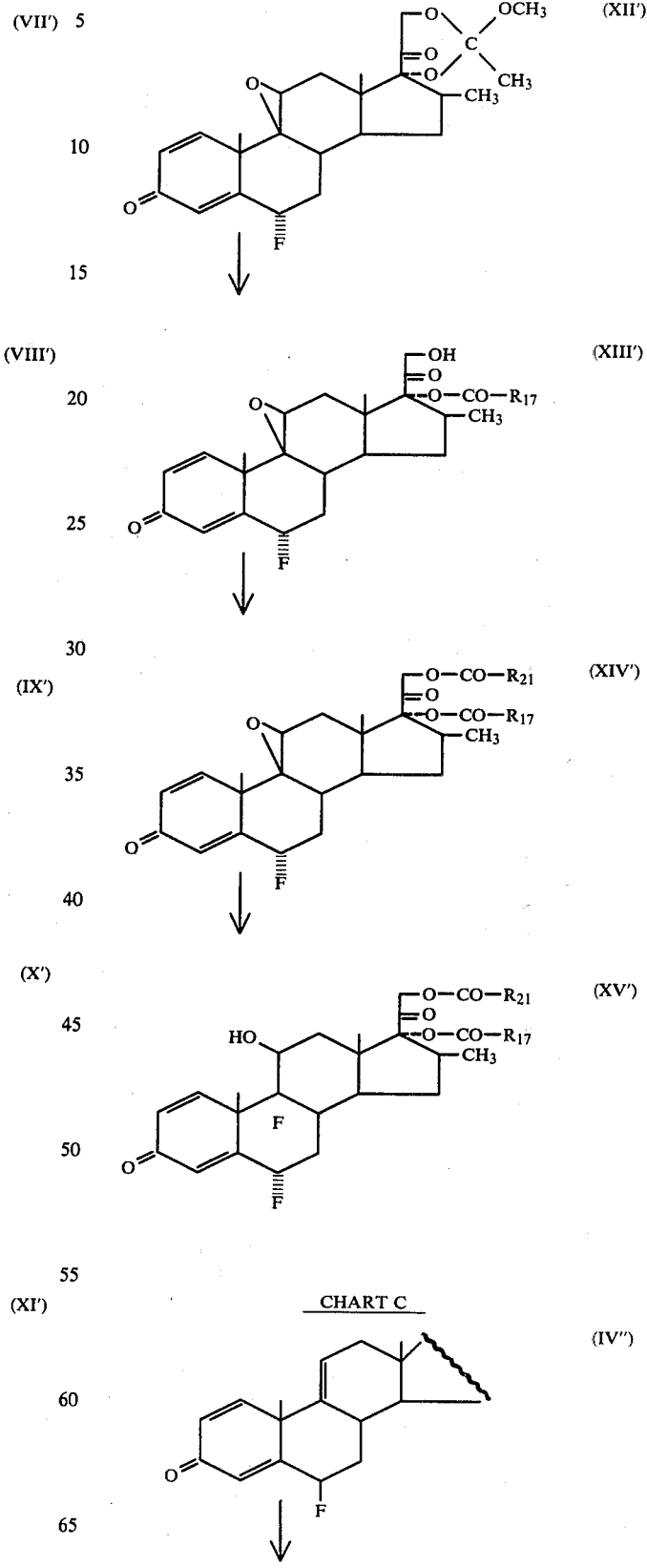
CHART C

-continued
CHART C
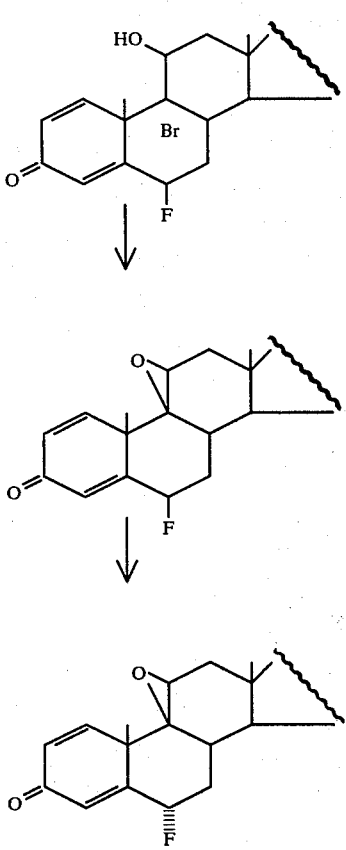
(Xβ)
(E)
(XI)
CHART D
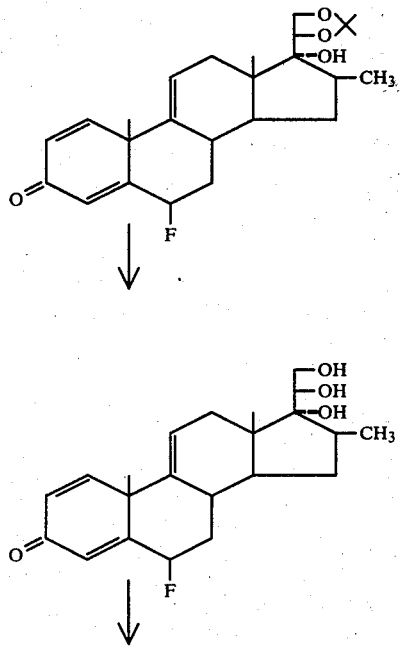
(IV′)
(VIβ′)
-continued
CHART D
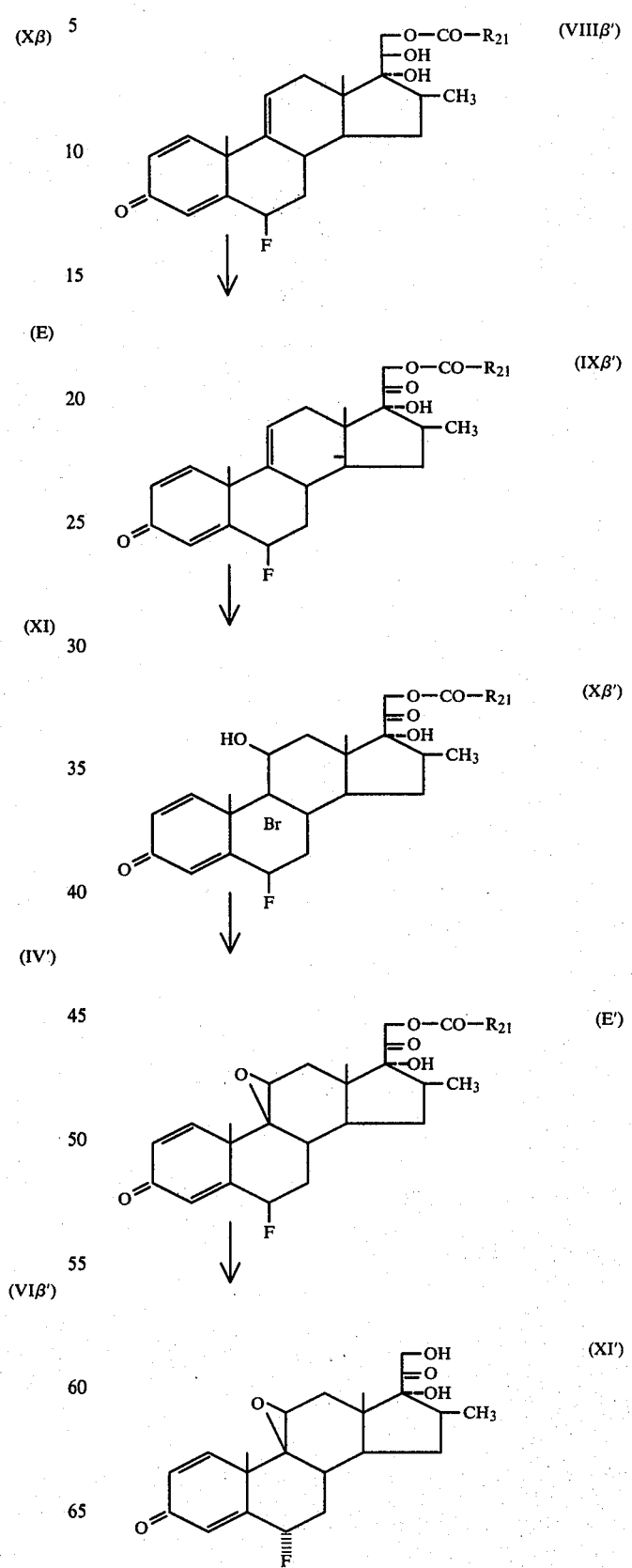
(VIIIβ′)
(IXβ′)
(Xβ′)
(E′)
(XI′)

CHART E

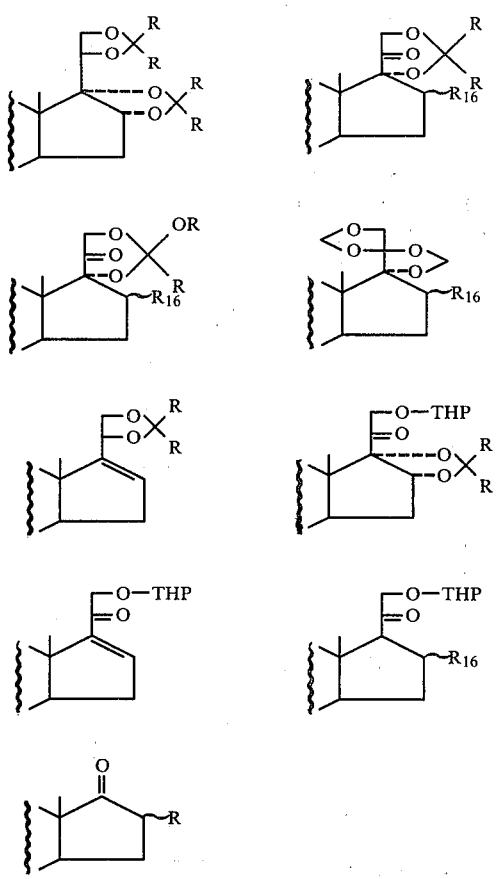

I claim:

1. A process for preparing a 6α-fluoro-$\Delta^{1,4}$-3-keto steroid of the formula

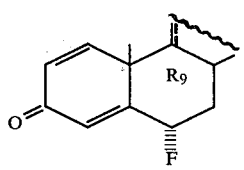
(VI)

which comprises (1) deconjugating a 6β-fluoro-$\Delta^{1,4}$-3-keto steroid of the formula

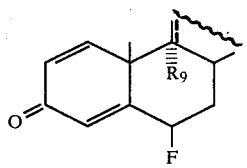
(IV)

by reaction with a deconjugating agent, (2) quenching with a quenching agent to produce a 6-fluoro-$\Delta^{1,5}$-3-keto steroid of the formula

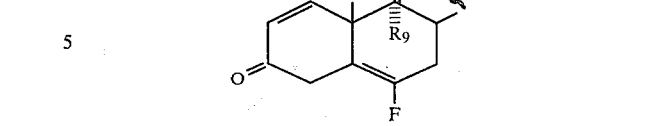
(V)

(3) isolating the 6-fluoro-$\Delta^{1,5}$-3-keto steroid (V)

(4) isomerizing the 6-fluoro-$\Delta^{1,5}$-3-keto steroid (V) by reaction with an isomerizing agent and (5) neutralizing with an acid where $R_9$ and $\rightleftharpoons$ are defined in the specification.

2. A process according to claim 1 where the deconjugating agent is selected from the group consisting of $ORb^\ominus$, acetylide or $R\alpha R\beta N^\ominus$ or a means of producing $ORB^\ominus$, acetylide or $R\alpha R\beta N^\ominus$ where Rb, Rα and Rβ are defined in the specification.

3. A process according to claim 2 where the deconjugating agent is selected from the group consisting of methoxide, ethoxide or tert-butoxide.

4. A process according to claim 1 where the solvent is selected from the group consisting of tert-butanol, THF, DMSO, dioxane, DMF, tetramethylurea and dimethylacetamide.

5. A process according to claim 4 where the deconjugating agent and solvent are tert-butoxide in tert-butanol.

6. A process according to claim 1 where the quenching agent is a compound which will supply a proton.

7. A process according to claim 6 where the quenching agent is selected from the group consisting of acetic acid, aqueous ammonium chloride, sulfuric acid, hydrochloric acid, phosphoric acid and water.

8. A process according to claim 7 where the quenching agent is acetic acid or aqueous ammonium chloride.

9. A process according to claim 1 where the isomerizing agent is selected from the group consisting of $ORb^\ominus$ or hydroxide or a means of producing $ORb^\ominus$ or hydroxide where Rb is defined in the specification.

10. A process according to claim 9 where the isomerizing agent is selected from the group consisting of methoxide, ethoxide, and isopropoxide.

11. A process according to claim 10 where the isomerizing agent is methoxide in methanol or ethoxide in ethanol.

12. A process according to claim 1 where the acid is selected from the group consisting of acetic, hydrochloric, sulfuric, phosphoric, and ammonium chloride.

13. A process according to claim 1 where the 6α-fluoro-$\Delta^{1,4}$-3-keto steroid (VI) is 6α-fluoro-17α,20,21-trihydroxy-16β-methylpregan-1,4,9(11)-trien-3-one 20,21-acetonide.

14. A process according to claim 1 where $\rightleftharpoons$ in the C ring is 9β,11β-epoxide, $\Delta^{9(11)}$- double bond, 11β-hydroxy, 11-keto, 11α-hydroxy or 9α-fluoro-11β-hydroxy.

15. A process according to claim 14 where $\rightleftharpoons$ in the C ring is a 9β,11β-epoxide or a $\Delta^{9(11)}$-double bond.

16. A process according to claim 1 where the D ring and the $C_{17}$ side chain are selected from the group consisting of

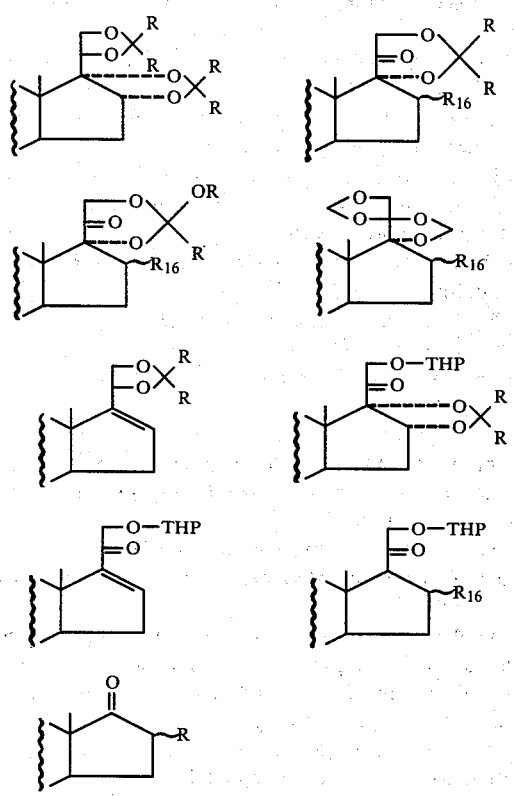

where R, $R_{16}$, THP and ~ are defined in the specification.

17. A process for preparing a 6-fluoro-$\Delta^{1,5}$-3-keto steroid of the formula

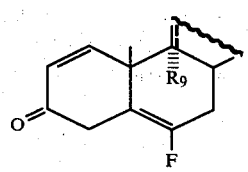

(V)

which comprises
(1) deconjugating a 6β-fluoro-$\Delta^{1,4}$-3-keto steroid of the formula

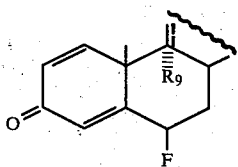

(IV)

by reaction with a deconjugating agent,
(2) quenching with a quenching agent and
(3) isolating the 6-fluoro-$\Delta^{1,5}$-3-keto steroid (V) where $R_9$ and    are defined in the specification.

18. A process according to claim 17 where the deconjugating agent is selected from the group consisting of ORb⊖, acetylide or RαRβN⊖ or a means of producing ORb⊖, acetylide or RαRβN⊖ where Rb, Rα and Rβ are defined in the specification.

19. A process according to claim 18 where the deconjugating agent is selected from the group consisting of methoxide, ethoxide or tertbutoxide, or a means of producing the same.

20. A process according to claim 17 where the solvent is selected from the group consisting of tert-butanol, THF, DMSO, and dioxane, DMF, tetramethylurea and dimethylacetamide.

21. A process according to claim 20 where the deconjugating agent and solvent are tert-butoxide in tert-butanol.

22. A process according to claim 15 where the quenching agent is a compound which will supply a proton.

23. A process according to claim 20 where the quenching agent is selected from the group consisting of acetic acid, aqueous ammonium chloride, sulfuric acid, hydrochloric acid, phosphoric acid and water.

24. A process according to claim 21 where the quenching agent is acetic acid or aqueous ammonium chloride.

25. A process according to claim 17 where the 6-fluoro-$\Delta^{1,5}$-3-keto steroid (V) is 6-fluoro-17α,20,21-trihydroxy-16β-methylpregna-1,5,9(11)-trien-3-one 20-21-acetonide.

26. A process according to claim 17 where    in the C ring is 9β,11β-epoxide, $\Delta^{9(11)}$-double bond, 11β-hydroxy, 11-keto, 11α-hydroxy or 9α-fluoro-11β-hydroxy.

27. A process according to claim 17 where    in the C ring is a 9β,11β-epoxide or a $\Delta^{9(11)}$-double bond.

28. A process according to claim 17 where the D ring and the $C_{17}$ side chain are selected from the group consisting of

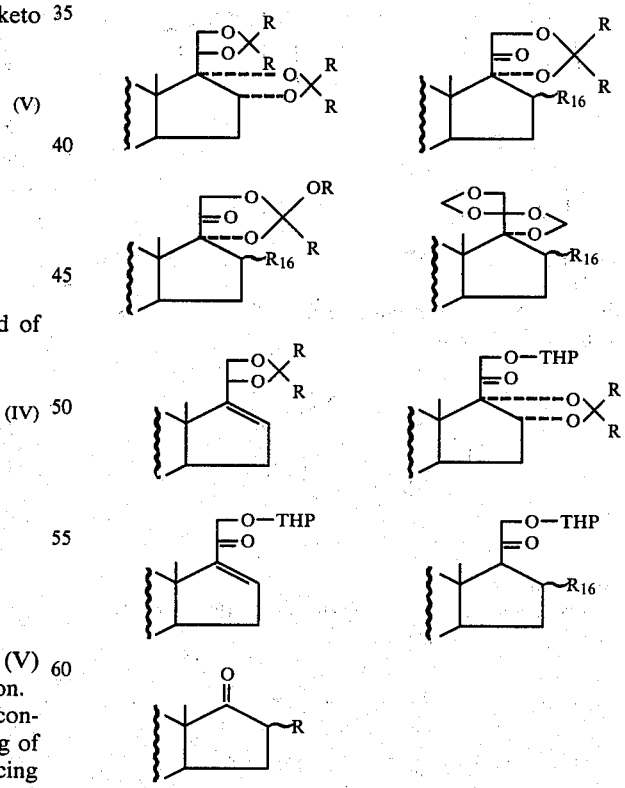

where R, $R_{16}$, THP and ~ are defined in the specification.

29. A 6-fluoro-$\Delta^{1,5}$-3-keto steroid of the formula

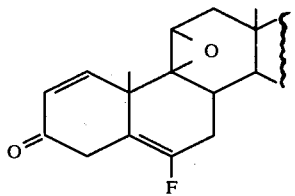
(Ve)

where the D ring and the $C_{17}$ side chain are selected from the group consisting of

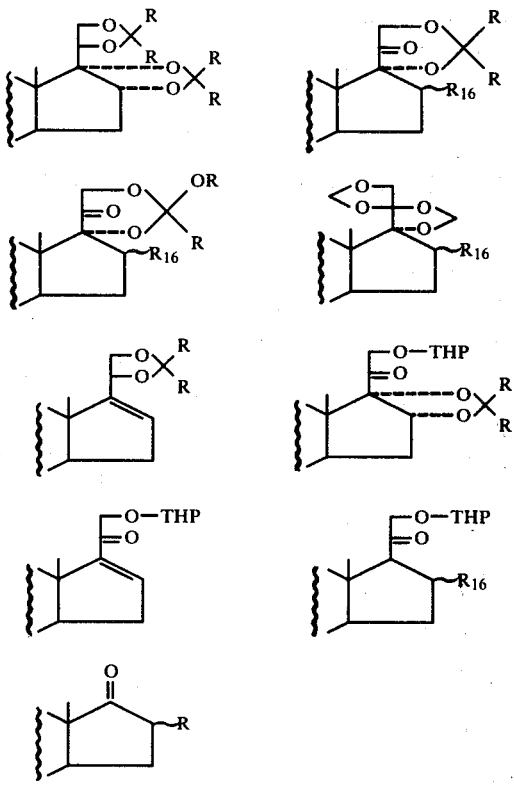

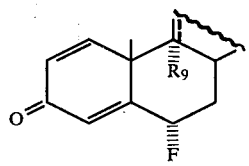

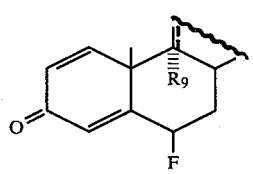

where R, $R_9$, $R_{16}$, THP, and ~ are defined in the specification.

30. A process for preparing a 6α-fluoro-$\Delta^{1,4}$-3-keto steroid of the formula (VI)

which comprises
(1) mixing a 6β-$\Delta^{1,4}$-3-keto steroid of the formula (IV)

with an deconjugating agent in the presence of a solvent selected from the group consisting of THF, DMSO, DMF, dimethylacetamide, dioxane, tert-butanol and tert-amyl alcohol,
(2) mixing with a primary or secondary alcohol of the formula Rb-OH and
(3) neutralizing with an acid where $R_g$, Rb and ~ are defined in the specification.

31. A process according to claim 30 where the deconjugating agent is selected from the group consisting of ORb$^\ominus$, acetylide or Rα Rβ N$^\ominus$ pr a means of producting ORb$^\ominus$, acetylide or Rα Rβ N$^\ominus$ where Rb, Rα and Rβ are defined in the specification.

32. A process according to claim 31 where the deconjugating agent is selected from the group consisting of methoxide, ethoxide or tertbutoxide, or a means of producing the same.

33. A process according to claim 30 where the primary or secondary alcohol is selected from the group consisting of methanol, ethanol, m-propanol, isopropanol or n-butanol.

34. A process according to claim 30 where the primary or secondary alcohol is methanol, ethanol or isopropanol.

35. A process according to claim 33 where the acid is selected from the group consisting of acetic, hydrochloric, sulfuric, phosphoric and ammonium chloride.

36. A process according to claim 33 where the 6α-fluoro-$\Delta^{1,4}$-3-keto steroid (VI) is 6α-fluoro-17α,20,21-trihydroxy-16β-methylpregna-1,4,9(11)-trien-3-one 20,21-acetonide.

37. A process according to claim 33 where ~ in the C ring is 9β,11β-epoxide, $\Delta^{9(11)}$-double bond, 11β-hydroxy, 11-keto, 11α-hydroxy or 9α-fluoro-11β-hydroxy.

38. A process according to claim 1 where ~ in the C ring is a 9β,11β-epoxide or a $\Delta^{9(11)}$-double bond.

39. A process according to claim 30 where the D ring and the $C_{17}$ side chain are selected from the group consisting of

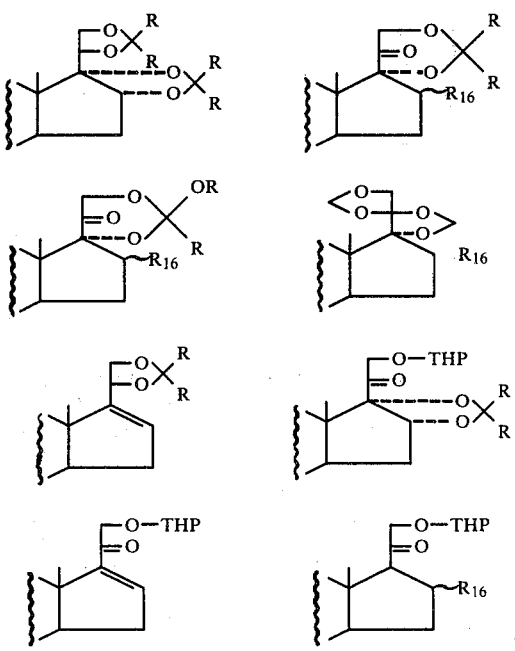

-continued

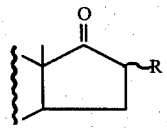

where R, $R_{16}$, THP and $\sim$ are defined in the specification.

40. A process for preparing a 6α-fluoro-$\Delta^{1,4}$-3-keto steroid of the formula

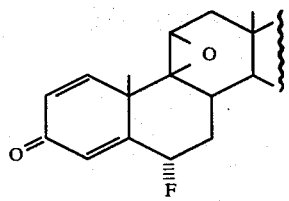

(VIe)

which comprises
(1) mixing a 6β-fluoro-$\Delta^{1,4}$-3-keto steroid of the formula

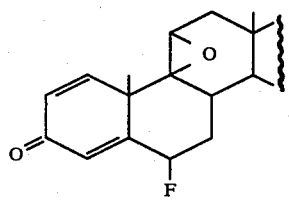

(IVe)

with an epimerizing agent in the presence of a primary or secondary alcohol of the formula Rb-OH and
(2) neutralizing with an acid where $R_9$, Rb and $\sim$ are defined in the specification.

41. A process according to claim 40 where the epimerizing agent is selected from the group consisting of $ORb^\ominus$, acetylide or $R\alpha R\beta N^\ominus$ or a means of producing $ORb^\ominus$, acetylide or $R\alpha R\beta N^\ominus$ where Rb, Rα and Rβ are defined in the specification.

42. A process according to claim 39 where the epimerizing agent is selected from the group consisting of methoxide, ethoxide or tertbutoxide.

43. A process according to claim 40 where the primary or secondary alcohol is selected from the group consisting of methanol, ethanol, m-propanol, isopropanol or n-butanol.

44. A process according to claim 43 where the primary or secondary alcohol is methanol, ethanol or isopropanol.

45. A process according to claim 40 where the acid is selected from the group consisting of acetic, hydrochloric, sulfuric, phosphoric and ammonium chloride.

46. A process according to claim 40 where the D ring and the $C_{17}$ side chain are selected from the group consisting of

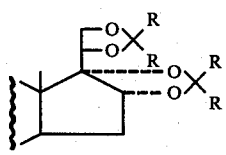 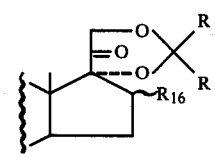

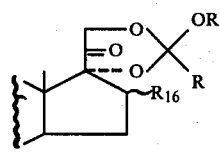 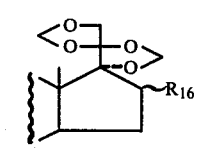

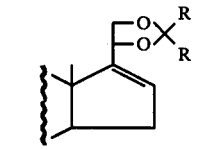 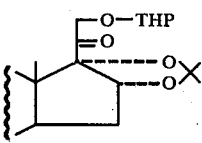

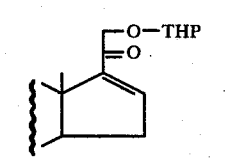 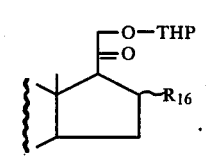

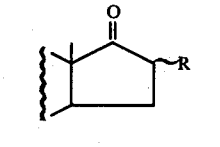

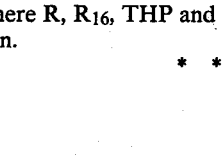

where R, $R_{16}$, THP and $\sim$ are defined in the specification.

* * * * *

Disclaimer 4,340,538.—*Kenneth P. Shepard*, Portage, Mich. PROCESS FOR PRODUCING 6 ALPHA-FLUORO-DELTA 1, 4-3-KETO STEROIDS. Patent dated July 20, 1982. Disclaimer filed June 8, 1983, by the assignee, *The Upjohn Co.*

Hereby enters this disclaimer to claim 29 of said patent.

[*Official Gazette October 11, 1983.*]

UNITED STATES PATENT OFFICE
CERTIFICATE OF CORRECTION

Patent No. 4,340,538                    Dated July 20, 1982

Inventor(s)   Kenneth P. Shephard

It is certified that error appears in the above-identified patent and that said Letters Patent are hereby corrected as shown below:

Col. 6, line 61: "... washed wth ..." should read: --washed with--.
Col. 7, lines 58-59: "rise to 25°.         should read: --rise to 25°. The
                     The mixture..."  mixture...--.  (There is no
new paragraph here).
Col. 10, lines 30-35, Formula IV, Chart A: Formula IV should appear as
        follows instead of as in the patent:  (portion)

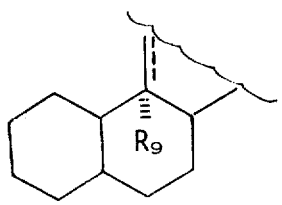

Col. 10, Chart A, Formula V: Formula V should appear as follows instead of as in the patent: (portion)

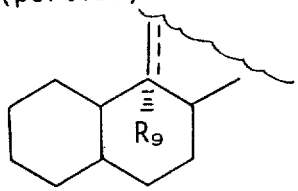

Col. 10, Chart A, Formula VI: Formula VI should appear as follows instead of as in the patent: (portion)

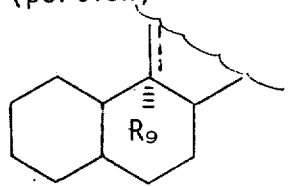

UNITED STATES PATENT OFFICE
CERTIFICATE OF CORRECTION   Page 2 of 4

Patent No. 4,340,538                    Dated  July 20, 1982

Inventor(s)  Kenneth P. Shephard

It is certified that error appears in the above-identified patent and that said Letters Patent are hereby corrected as shown below:

Col. 11, Chart B, Formula X': Formula X' should appear as follows instead of as in the patent: (portion)

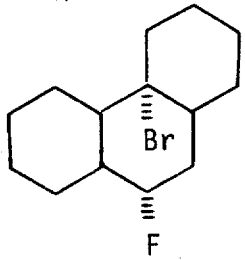

Col. 12, Chart C, Formula XV': Formula XV' should appear as follows instead of as in the patent: (portion)

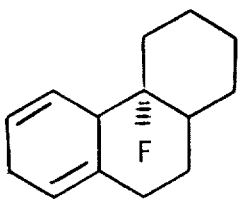

Col. 13, Chart C, Formula Xβ: Formula Xβ should appear as follows instead of as in the patent: (portion)

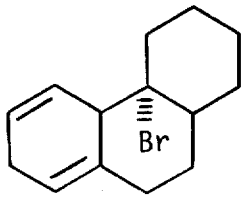

UNITED STATES PATENT OFFICE
CERTIFICATE OF CORRECTION

Patent No. 4,340,538  Dated July 20, 1982

Inventor(s) Kenneth P. Shephard

It is certified that error appears in the above-identified patent and that said Letters Patent are hereby corrected as shown below:

Col. 14, Chart D, Formula $X_\beta'$: Formula $X_\beta'$ should appear as follows instead of as in the patent: (portion)

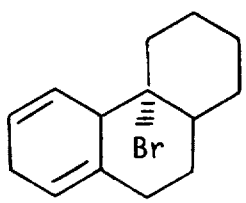

Col. 15, Claim 1, Formula VI: Formula VI should appear as follows instead of as in the patent: (portion)

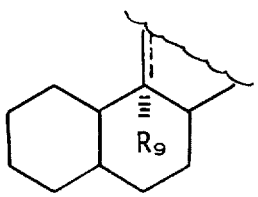

Col. 16, line 19: "$ORB^\ominus$" should read: --$ORb^\ominus$--.
Col. 18, Claim 26, line 25: "...where    in the ..." should read: --...where --- in the ...--.
Col. 18, Claim 27, line 29: '...where    in the ..." should read: --...where --- in the ...--.
Col. 19, Claim 29, line 44: "... THP,    and ..." should read: --... THP, .... and ...--.

UNITED STATES PATENT OFFICE
CERTIFICATE OF CORRECTION

Patent No. 4,340,538  Dated July 20, 1982

Inventor(s) Kenneth P. Shephard

It is certified that error appears in the above-identified patent and that said Letters Patent are hereby corrected as shown below:

Col. 20, Claim 39, lines 50-55, far right formula should appear as follows instead of as in the patent: (portion)

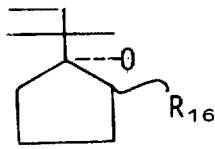

Col. 21, Claim 40, line 38: "... and        are . ." should read: "... and .... are ...--.

Signed and Sealed this

Third Day of July 1984

[SEAL]

Attest:

GERALD J. MOSSINGHOFF

Attesting Officer      Commissioner of Patents and Trademarks